United States Patent
Qiu et al.

(10) Patent No.: US 8,684,963 B2
(45) Date of Patent: Apr. 1, 2014

(54) CATHETER WITH A DUAL LUMEN MONOLITHIC SHAFT

(75) Inventors: Hua Qiu, Temecula, CA (US); Tung-Liang Lin, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 13/542,129

(22) Filed: Jul. 5, 2012

(65) Prior Publication Data
US 2014/0012193 A1    Jan. 9, 2014

(51) Int. Cl.
*A61M 29/00*    (2006.01)

(52) U.S. Cl.
USPC .................................................. 604/96.01

(58) Field of Classification Search
USPC ............ 604/96.01, 103.01, 103.08, 103.11
See application file for complete search history.

(56) References Cited

U.S. PATENT DOCUMENTS

| | | |
|---|---|---|
| 4,425,919 A | 1/1984 | Alston, Jr. et al. |
| 4,563,181 A | 1/1986 | Wijayarathna et al. |
| 4,596,563 A | 6/1986 | Pande |
| 4,748,982 A | 6/1988 | Horzewski et al. |
| 4,775,371 A | 10/1988 | Mueller, Jr. |
| 4,782,834 A | 11/1988 | Maguire et al. |
| 4,820,349 A | 4/1989 | Saab et al. |
| 4,877,031 A | 10/1989 | Conway et al. |
| 4,886,506 A | 12/1989 | Lovgren et al. |
| 4,892,519 A | 1/1990 | Songer et al. |
| 4,952,357 A | 8/1990 | Euteneuer |
| 4,976,690 A | 12/1990 | Solar et al. |
| 4,976,720 A | 12/1990 | Machold et al. |
| 5,047,045 A | 9/1991 | Arney et al. |
| 5,061,273 A | 10/1991 | Yock |
| 5,078,702 A | 1/1992 | Pomeranz |
| 5,085,649 A | 2/1992 | Flynn |
| 5,112,304 A | 5/1992 | Barlow et al. |

(Continued)

FOREIGN PATENT DOCUMENTS

| | | |
|---|---|---|
| EP | 0 277 368 | 8/1988 |
| EP | 0414350 | 2/1991 |

(Continued)

OTHER PUBLICATIONS

Levy, et al., "Plastics Extrusion Technology Handbook", Second Edition, Industrial Press, 1989.
Cordis' Product Brochure; The Journey Inspires the Design, AQUA T3, Dec. 2002.
The Manufacturing Process Section of the Phelps Dodge High Performance Conductors Brochure, a Primer on Polymide Tubing, pp. 1. http://www.zeusinc.com/peek_resin.asp.

(Continued)

*Primary Examiner* — Aarti B Berdichevsky
(74) *Attorney, Agent, or Firm* — Baker Botts L.L.P.

(57) ABSTRACT

Multi-lumen catheter having a monolithic elongate tubular shaft member having a proximal end, a distal end and a longitudinal length therebetween. The tubular shaft member has an outer cross-sectional dimension that varies along the length of the tubular shaft member. The tubular shaft member has an inner core made of a first material and an outer layer made of a second material. The inner core has a first lumen and a second lumen defined therein, the first lumen having a first lumen cross-section and a length extending at least along a portion of the length of the tubular shaft member. The first lumen cross-section is substantially uniform along the length of the first lumen. The second lumen has a second lumen cross-section and a length extending along the length of tubular shaft member. The second lumen cross-section is substantially uniform along the length of the second lumen.

32 Claims, 6 Drawing Sheets

(56) References Cited

U.S. PATENT DOCUMENTS

| | | | |
|---|---|---|---|
| 5,156,594 A | 10/1992 | Keith |
| 5,176,661 A | 1/1993 | Evard et al. |
| 5,195,969 A | 3/1993 | Wang et al. |
| 5,205,822 A | 4/1993 | Johnson et al. |
| 5,207,700 A | 5/1993 | Euteneuer |
| 5,217,434 A | 6/1993 | Arney |
| 5,217,482 A | 6/1993 | Keith |
| 5,250,059 A | 10/1993 | Andreas et al. |
| 5,270,086 A | 12/1993 | Hamlin |
| 5,277,199 A | 1/1994 | DeBois et al. |
| 5,290,232 A | 3/1994 | Johnson et al. |
| 5,290,306 A | 3/1994 | Trotta et al. |
| 5,300,025 A | 4/1994 | Wantink |
| 5,300,085 A | 4/1994 | Yock |
| 5,304,134 A | 4/1994 | Kraus et al. |
| 5,312,430 A | 5/1994 | Rosenbluth et al. |
| 5,318,032 A | 6/1994 | Lonsbury et al. |
| 5,318,526 A | 6/1994 | Cohen |
| 5,342,386 A | 8/1994 | Trotta |
| 5,358,486 A | 10/1994 | Saab |
| 5,364,357 A | 11/1994 | Aase |
| 5,370,655 A | 12/1994 | Burns |
| 5,378,238 A | 1/1995 | Peters et al. |
| 5,395,336 A | 3/1995 | Barclay et al. |
| 5,423,754 A | 6/1995 | Cornelius et al. |
| 5,425,712 A | 6/1995 | Goodin |
| 5,447,497 A | 9/1995 | Sogard et al. |
| 5,451,233 A | 9/1995 | Yock |
| 5,454,789 A | 10/1995 | Burns et al. |
| 5,458,615 A | 10/1995 | Klemm et al. |
| 5,464,650 A | 11/1995 | Berg et al. |
| 5,470,315 A | 11/1995 | Adams |
| 5,476,477 A | 12/1995 | Burns |
| 5,478,320 A | 12/1995 | Trotta |
| 5,484,409 A | 1/1996 | Atkinson et al. |
| 5,490,837 A | 2/1996 | Blaeser et al. |
| 5,496,275 A | 3/1996 | Sirhan et al. |
| 5,496,346 A | 3/1996 | Horzewski et al. |
| 5,499,980 A | 3/1996 | Euteneuer |
| 5,507,768 A | 4/1996 | Lau et al. |
| 5,512,051 A | 4/1996 | Wang et al. |
| 5,526,823 A | 6/1996 | Wheeler et al. |
| 5,538,513 A | 7/1996 | Okajima |
| 5,542,937 A * | 8/1996 | Chee et al. ................... 604/523 |
| 5,545,134 A | 8/1996 | Hilaire et al. |
| 5,545,138 A | 8/1996 | Fugoso et al. |
| 5,549,552 A | 8/1996 | Peters et al. |
| 5,554,121 A | 9/1996 | Ainsworth et al. |
| 5,556,383 A | 9/1996 | Wang et al. |
| 5,569,195 A | 10/1996 | Saab |
| 5,587,125 A | 12/1996 | Roychowdhury |
| 5,591,227 A | 1/1997 | Dinh et al. |
| 5,599,326 A | 2/1997 | Carter |
| 5,613,979 A | 3/1997 | Trotta et al. |
| 5,620,649 A | 4/1997 | Trotta |
| 5,622,665 A | 4/1997 | Wang |
| 5,626,600 A | 5/1997 | Horzewski et al. |
| 5,632,760 A | 5/1997 | Sheiban et al. |
| 5,643,209 A | 7/1997 | Fugoso et al. |
| 5,649,909 A | 7/1997 | Cornelius |
| 5,649,977 A | 7/1997 | Campbell |
| 5,658,264 A | 8/1997 | Samson |
| 5,690,613 A | 11/1997 | Verbeek |
| 5,728,063 A | 3/1998 | Preissman et al. |
| 5,743,874 A | 4/1998 | Fischell et al. |
| 5,743,875 A | 4/1998 | Sirhan et al. |
| 5,749,849 A | 5/1998 | Engelson |
| 5,755,690 A | 5/1998 | Saab |
| 5,759,173 A | 6/1998 | Preissman et al. |
| 5,766,151 A | 6/1998 | Valley et al. |
| 5,769,817 A | 6/1998 | Burgmeier |
| 5,769,819 A | 6/1998 | Schwab et al. |
| 5,775,327 A | 7/1998 | Randolph et al. |
| 5,779,731 A | 7/1998 | Leavitt |
| 5,782,811 A | 7/1998 | Samson et al. |
| 5,791,036 A | 8/1998 | Goodin et al. |
| 5,792,124 A | 8/1998 | Horrigan et al. |
| 5,792,144 A | 8/1998 | Fischell et al. |
| 5,795,325 A | 8/1998 | Valley et al. |
| 5,795,341 A | 8/1998 | Samson |
| 5,797,887 A | 8/1998 | Rosen et al. |
| 5,814,016 A | 9/1998 | Valley et al. |
| 5,820,594 A | 10/1998 | Fontirroche et al. |
| 5,833,657 A | 11/1998 | Reinhardt et al. |
| 5,879,369 A | 3/1999 | Ishida |
| 5,879,499 A | 3/1999 | Corvi |
| 5,902,290 A | 5/1999 | Peacock et al. |
| 5,908,406 A | 6/1999 | Ostapchenko et al. |
| 5,911,715 A | 6/1999 | Berg et al. |
| 5,916,193 A | 6/1999 | Stevens et al. |
| 5,947,939 A | 9/1999 | Mortier et al. |
| 5,964,778 A | 10/1999 | Fugoso et al. |
| 6,004,289 A | 12/1999 | Saab |
| 6,004,339 A | 12/1999 | Wijay |
| 6,010,521 A | 1/2000 | Lee et al. |
| 6,021,340 A | 2/2000 | Randolph et al. |
| 6,024,693 A | 2/2000 | Schock et al. |
| 6,024,722 A | 2/2000 | Rau et al. |
| 6,027,510 A | 2/2000 | Alt |
| 6,036,670 A | 3/2000 | Wijeratne et al. |
| 6,056,719 A | 5/2000 | Mickley |
| 6,059,751 A | 5/2000 | Ostapchenko et al. |
| 6,059,770 A | 5/2000 | Peacock et al. |
| 6,071,266 A | 6/2000 | Kelley |
| 6,086,556 A | 7/2000 | Hamilton et al. |
| 6,102,890 A | 8/2000 | Stivland et al. |
| 6,124,007 A | 9/2000 | Wang et al. |
| 6,132,824 A | 10/2000 | Hamlin |
| 6,136,258 A | 10/2000 | Wang et al. |
| 6,146,356 A | 11/2000 | Wang et al. |
| 6,165,166 A | 12/2000 | Samuelson et al. |
| 6,165,195 A | 12/2000 | Wilson et al. |
| 6,171,275 B1 | 1/2001 | Webster, Jr. |
| 6,171,278 B1 | 1/2001 | Wang et al. |
| 6,179,810 B1 | 1/2001 | Wantink et al. |
| 6,179,856 B1 | 1/2001 | Barbere |
| 6,193,686 B1 | 2/2001 | Estrada et al. |
| 6,210,396 B1 | 4/2001 | MacDonald et al. |
| 6,217,565 B1 | 4/2001 | Cohen |
| 6,242,063 B1 | 6/2001 | Ferrera et al. |
| 6,245,053 B1 | 6/2001 | Benjamin |
| 6,251,093 B1 | 6/2001 | Valley et al. |
| 6,264,683 B1 | 7/2001 | Stack et al. |
| 6,265,016 B1 | 7/2001 | Hostettler et al. |
| 6,287,285 B1 | 9/2001 | Michal et al. |
| 6,306,097 B1 | 10/2001 | Park et al. |
| 6,306,124 B1 | 10/2001 | Jones et al. |
| 6,308,342 B1 | 10/2001 | Qi |
| 6,358,227 B1 | 3/2002 | Ferrera et al. |
| 6,364,894 B1 | 4/2002 | Healy et al. |
| 6,406,457 B1 | 6/2002 | Wang et al. |
| 6,416,494 B1 | 7/2002 | Wilkins |
| 6,482,348 B1 | 11/2002 | Wang et al. |
| 6,495,090 B1 | 12/2002 | Wilkins |
| 6,495,127 B1 | 12/2002 | Wallace et al. |
| 6,500,148 B1 | 12/2002 | Pinchuk et al. |
| 6,508,784 B1 | 1/2003 | Shu |
| 6,541,116 B2 | 4/2003 | Michal et al. |
| 6,575,934 B2 | 6/2003 | Duchamp |
| 6,575,958 B1 | 6/2003 | Happ et al. |
| 6,579,259 B2 | 6/2003 | Stevens et al. |
| 6,585,687 B1 | 7/2003 | Shkolnik |
| 6,585,688 B2 | 7/2003 | Ferrera et al. |
| 6,589,207 B1 | 7/2003 | El-Nounou |
| 6,589,226 B1 | 7/2003 | Owens |
| 6,620,127 B2 | 9/2003 | Lee et al. |
| 6,620,128 B1 | 9/2003 | Simhambhatla |
| 6,626,889 B1 | 9/2003 | Simpson et al. |
| 6,629,961 B1 | 10/2003 | Israelsson et al. |
| 6,645,422 B2 | 11/2003 | Jung, Jr. et al. |
| 6,663,614 B1 | 12/2003 | Carter |
| 6,669,980 B2 | 12/2003 | Hansen |
| 6,673,291 B1 | 1/2004 | Field et al. |
| 6,673,302 B2 | 1/2004 | Wang et al. |

(56) References Cited

U.S. PATENT DOCUMENTS

| | | |
|---|---|---|
| 6,695,809 B1 | 2/2004 | Lee |
| 6,702,802 B1 | 3/2004 | Hancock et al. |
| 6,718,211 B2 | 4/2004 | Smits |
| 6,733,487 B2 | 5/2004 | Keith et al. |
| 6,756,094 B1 | 6/2004 | Wang et al. |
| 6,777,644 B2 | 8/2004 | Peacock et al. |
| 6,793,647 B1 | 9/2004 | Cryer et al. |
| 6,796,958 B2 | 9/2004 | Chen et al. |
| 6,796,960 B2 | 9/2004 | Cioanta et al. |
| 6,835,189 B2 | 12/2004 | Musbach et al. |
| 6,837,890 B1 | 1/2005 | Chludzinski et al. |
| 6,863,678 B2 | 3/2005 | Lee et al. |
| 6,875,197 B1 | 4/2005 | Simhambhatla et al. |
| 6,887,219 B2 | 5/2005 | Wantink |
| 6,890,395 B2 | 5/2005 | Simhambhatla et al. |
| 6,893,456 B2 | 5/2005 | Lumauig |
| 6,911,038 B2 | 6/2005 | Mertens et al. |
| 6,913,600 B2 | 7/2005 | Valley et al. |
| 6,918,920 B1 | 7/2005 | Wang et al. |
| 6,923,822 B2 | 8/2005 | Crawford et al. |
| 6,946,092 B1 | 9/2005 | Bertolino et al. |
| 6,951,555 B1 | 10/2005 | Suresh et al. |
| 6,951,675 B2 | 10/2005 | Chin et al. |
| 6,964,750 B2 | 11/2005 | Fulford |
| 6,979,342 B2 | 12/2005 | Lee et al. |
| 7,026,026 B2 | 4/2006 | Ferrera et al. |
| 7,029,732 B2 | 4/2006 | Wang et al. |
| 7,037,291 B2 | 5/2006 | Lee et al. |
| 7,037,295 B2 | 5/2006 | Tieman et al. |
| 7,074,206 B2 | 7/2006 | Lee et al. |
| 7,108,877 B2 | 9/2006 | Blair et al. |
| 7,112,357 B2 | 9/2006 | Miller et al. |
| 7,141,059 B2 | 11/2006 | Duchamp et al. |
| 7,147,817 B1 | 12/2006 | Lim et al. |
| 7,163,523 B2 | 1/2007 | Devens, Jr. et al. |
| 7,195,638 B1 | 3/2007 | Sridharan |
| 7,241,344 B2 | 7/2007 | Worsham et al. |
| 7,273,485 B2 | 9/2007 | Simpson et al. |
| 7,273,487 B1 * | 9/2007 | Duchamp et al. ............. 606/194 |
| 7,303,798 B2 | 12/2007 | Bavaro et al. |
| 7,322,959 B2 | 1/2008 | Warnack et al. |
| 7,335,185 B2 | 2/2008 | Tang et al. |
| 7,335,227 B2 | 2/2008 | Jalisi |
| 7,378,105 B2 | 5/2008 | Burke et al. |
| 7,445,792 B2 | 11/2008 | Toner et al. |
| 7,549,975 B2 | 6/2009 | Lee et al. |
| 7,556,634 B2 | 7/2009 | Lee et al. |
| 7,662,130 B2 | 2/2010 | Lee et al. |
| 7,828,766 B2 | 11/2010 | Durcan |
| 7,833,193 B2 | 11/2010 | Lee et al. |
| 7,833,597 B2 | 11/2010 | Bavaro et al. |
| 7,850,675 B2 * | 12/2010 | Bell et al. ....................... 604/523 |
| 7,862,541 B2 | 1/2011 | Jeffrey et al. |
| 7,906,066 B2 | 3/2011 | Wilson et al. |
| 7,967,836 B2 | 6/2011 | Warnack et al. |
| 8,048,058 B2 | 11/2011 | Fulford |
| 8,052,638 B2 | 11/2011 | Lee et al. |
| 8,070,719 B2 | 12/2011 | Lee et al. |
| 2001/0001812 A1 | 5/2001 | Valley et al. |
| 2001/0029362 A1 | 10/2001 | Sirhan et al. |
| 2001/0037085 A1 | 11/2001 | Keith et al. |
| 2002/0018866 A1 | 2/2002 | Lee et al. |
| 2002/0082548 A1 * | 6/2002 | Sanchez et al. ............ 604/96.01 |
| 2002/0165523 A1 | 11/2002 | Chin et al. |
| 2003/0009151 A1 | 1/2003 | Wang |
| 2003/0055447 A1 | 3/2003 | Lee et al. |
| 2003/0078537 A1 | 4/2003 | Jang |
| 2003/0105426 A1 | 6/2003 | Jorgensen |
| 2003/0139762 A1 | 7/2003 | Lee |
| 2004/0039332 A1 | 2/2004 | Kantor |
| 2004/0059291 A1 | 3/2004 | McDonnell et al. |
| 2004/0059292 A1 | 3/2004 | Hisamatsu et al. |
| 2004/0064130 A1 | 4/2004 | Carter |
| 2004/0068240 A1 | 4/2004 | Goodin et al. |
| 2004/0092867 A1 * | 5/2004 | Murray, III .................... 604/103 |
| 2004/0131808 A1 | 7/2004 | Schoenle et al. |
| 2004/0170782 A1 | 9/2004 | Wang et al. |
| 2004/0173935 A1 | 9/2004 | Lim et al. |
| 2004/0181206 A1 | 9/2004 | Chiu et al. |
| 2004/0191443 A1 | 9/2004 | Hamlin |
| 2004/0215141 A1 | 10/2004 | Clarke et al. |
| 2004/0234748 A1 | 11/2004 | Stenzel |
| 2004/0267195 A1 | 12/2004 | Currlin |
| 2004/0267280 A1 | 12/2004 | Nishide et al. |
| 2005/0015048 A1 | 1/2005 | Chiu et al. |
| 2005/0043679 A1 | 2/2005 | Devens et al. |
| 2005/0124976 A1 | 6/2005 | Devens, Jr. et al. |
| 2005/0131445 A1 | 6/2005 | Holman et al. |
| 2005/0148997 A1 | 7/2005 | Valley et al. |
| 2005/0154414 A1 | 7/2005 | Perreault et al. |
| 2005/0186370 A1 | 8/2005 | Hamilton et al. |
| 2005/0228429 A1 | 10/2005 | Burgmeier et al. |
| 2005/0238833 A1 | 10/2005 | Wang et al. |
| 2005/0261725 A1 | 11/2005 | Crawford et al. |
| 2005/0277878 A1 | 12/2005 | Lee |
| 2006/0008606 A1 | 1/2006 | Horn et al. |
| 2006/0020256 A1 | 1/2006 | Bell et al. |
| 2006/0136032 A1 | 6/2006 | Legarda et al. |
| 2006/0165926 A1 | 7/2006 | Weber |
| 2006/0175739 A1 | 8/2006 | Hession et al. |
| 2006/0282041 A1 | 12/2006 | Melsheimer et al. |
| 2007/0021772 A1 | 1/2007 | von Oepen et al. |
| 2007/0060863 A1 | 3/2007 | Goeken et al. |
| 2007/0088255 A1 | 4/2007 | Toner et al. |
| 2007/0142771 A1 | 6/2007 | Durcan |
| 2007/0167973 A1 | 7/2007 | Stupecky et al. |
| 2007/0191813 A1 | 8/2007 | Chen |
| 2007/0240817 A1 | 10/2007 | Strong et al. |
| 2008/0015499 A1 | 1/2008 | Warnack |
| 2008/0045895 A1 | 2/2008 | Simpson et al. |
| 2008/0045928 A1 | 2/2008 | Simpson et al. |
| 2008/0065188 A1 | 3/2008 | Pallazza |
| 2008/0262470 A1 | 10/2008 | Lee et al. |
| 2009/0005754 A1 | 1/2009 | Soetermans |
| 2009/0036829 A1 | 2/2009 | Pagel et al. |
| 2009/0041923 A1 * | 2/2009 | Lin et al. ........................ 427/2.3 |
| 2009/0156998 A1 | 6/2009 | Arana et al. |
| 2009/0223624 A1 | 9/2009 | Lee et al. |
| 2009/0247946 A1 | 10/2009 | Lee et al. |
| 2009/0264822 A1 | 10/2009 | Johnson |
| 2010/0010439 A1 | 1/2010 | Burgmeier et al. |
| 2010/0023108 A1 | 1/2010 | Toner et al. |
| 2010/0030183 A1 | 2/2010 | Toner et al. |
| 2010/0063476 A1 * | 3/2010 | Quillin ........................ 604/523 |
| 2010/0130925 A1 | 5/2010 | Haslinger et al. |
| 2010/0189876 A1 | 7/2010 | Kokish et al. |
| 2010/0285085 A1 | 11/2010 | Stankus et al. |
| 2011/0022150 A1 | 1/2011 | Durcan |
| 2011/0028019 A1 | 2/2011 | Hwang |
| 2011/0034904 A1 * | 2/2011 | Stivland et al. ............... 604/524 |
| 2011/0070355 A1 | 3/2011 | Bavaro et al. |
| 2011/0143014 A1 | 6/2011 | Stankus et al. |
| 2011/0172696 A1 | 7/2011 | Jeffrey et al. |
| 2011/0315301 A1 | 12/2011 | Simpson et al. |
| 2012/0065586 A1 | 3/2012 | Lee et al. |
| 2012/0077049 A1 * | 3/2012 | Lin ............................... 428/520 |
| 2012/0128863 A1 | 5/2012 | Nguyen et al. |
| 2012/0143129 A1 | 6/2012 | Simpson et al. |
| 2013/0072906 A1 * | 3/2013 | Stivland et al. ............... 604/526 |
| 2013/0123664 A1 * | 5/2013 | Lin et al. ....................... 600/585 |

FOREIGN PATENT DOCUMENTS

| | | |
|---|---|---|
| EP | 0420488 | 3/1991 |
| EP | 0737487 | 10/1996 |
| EP | 0821979 | 2/1998 |
| EP | 0904795 | 3/1999 |
| EP | 0931558 | 7/1999 |
| EP | 0962227 | 8/1999 |
| JP | 10-290837 | 11/1998 |
| JP | 2001-353225 | 12/2001 |
| JP | 2005-167638 | 6/2005 |
| WO | WO 92/20379 | 11/1992 |
| WO | WO 93/15786 | 8/1993 |

(56) References Cited

FOREIGN PATENT DOCUMENTS

| WO | WO 93/20882 | 10/1993 |
| WO | WO 95/18647 | 7/1995 |
| WO | WO 96/03175 | 2/1996 |
| WO | WO 96/34646 | 11/1996 |
| WO | WO 99/13924 | 3/1999 |
| WO | WO 01/34240 | 5/2001 |
| WO | WO 01/43944 | 6/2001 |
| WO | WO 01/51115 | 7/2001 |
| WO | WO 01/89621 | 11/2001 |
| WO | WO 02/36196 | 5/2002 |
| WO | WO 2005/021083 | 3/2005 |
| WO | WO 2006/126311 | 11/2006 |

OTHER PUBLICATIONS www.sigmaaldrich.com/img/assets/3900/Thermal_Transitions_of_Homopolymers.pdf.

Etherington & Roberts Dictionary, http://Palimpsest.stanford.edu/don/dt/dt1549.html.

Polymers: Structure and Properties, C.A. Daniels, Ph.D., P.E.; Technomic Publishing Co., Inc.

International Search Report for PCT/US2010/037313, dated Apr. 28, 2011.

International Search Report and Written Opinion for PCT/US2013/045001, dated Sep. 4, 2013.

* cited by examiner

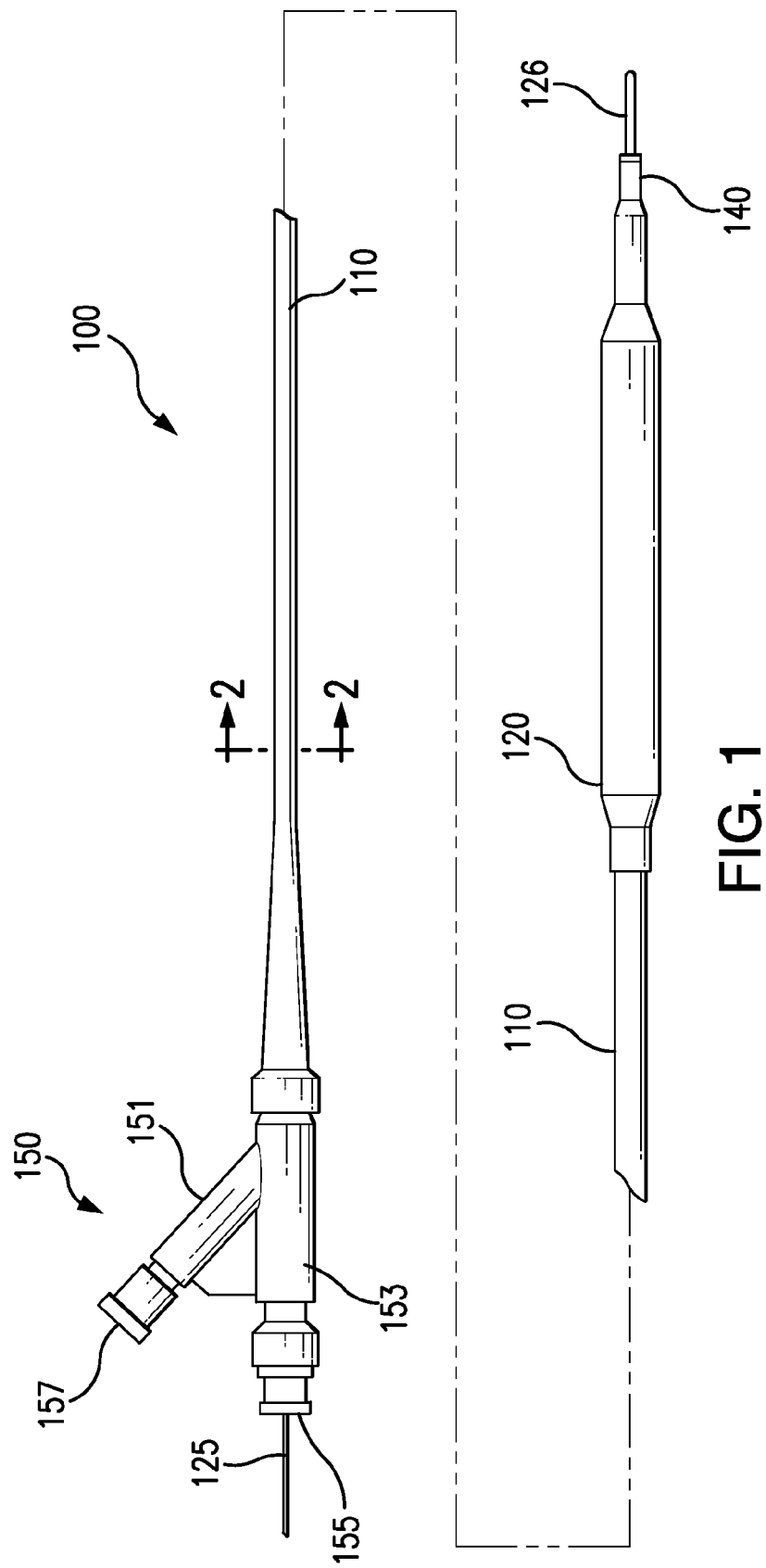

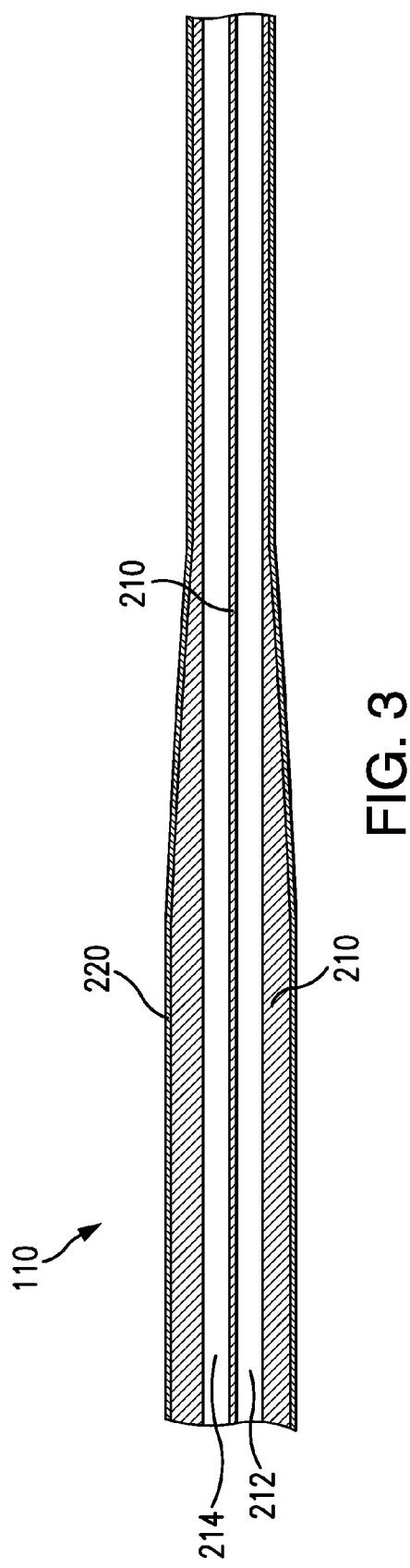
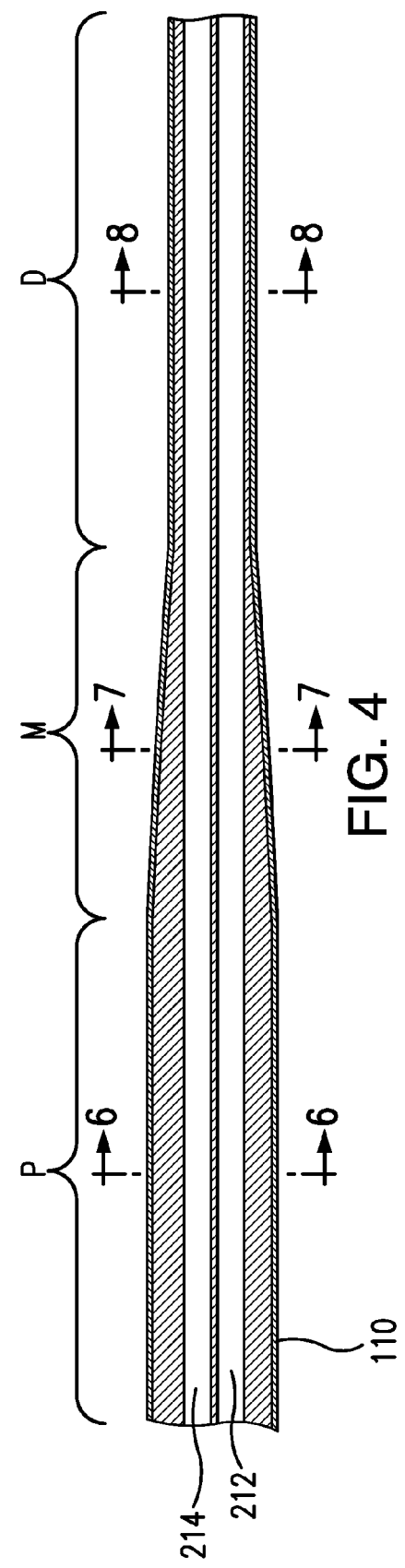

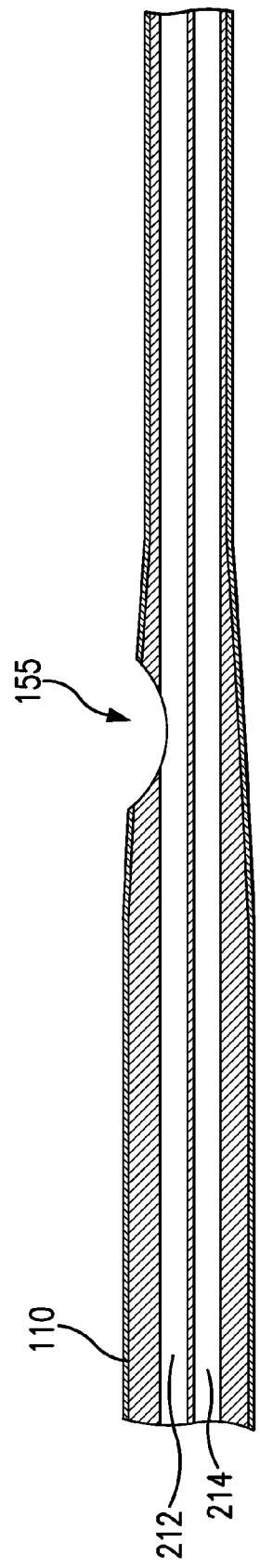
FIG. 5
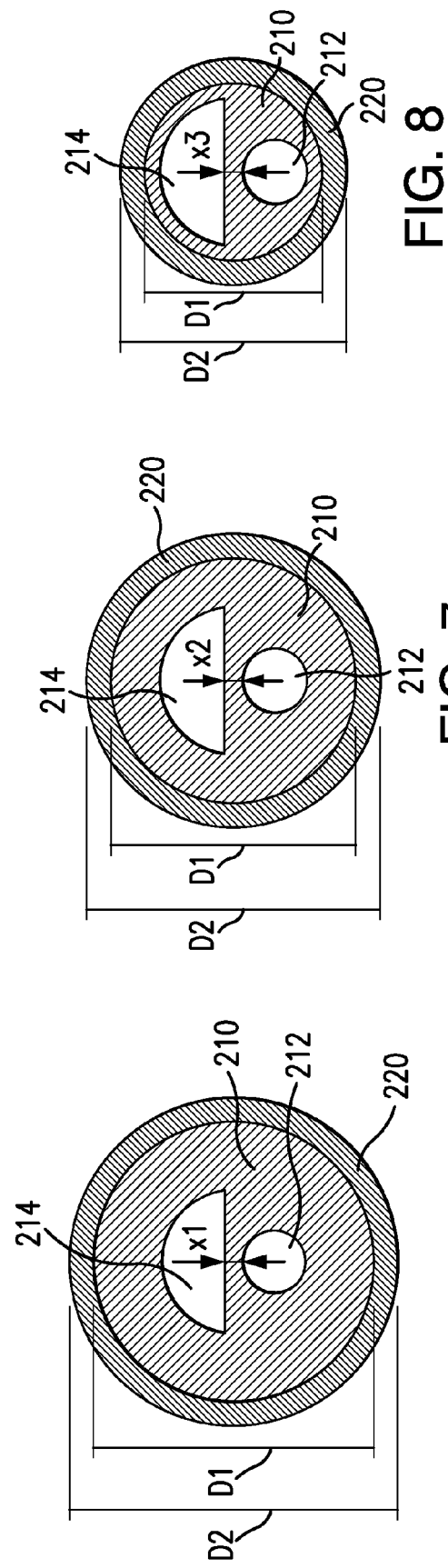
FIG. 6
FIG. 7
FIG. 8

CATHETER WITH A DUAL LUMEN MONOLITHIC SHAFT

BACKGROUND OF THE DISCLOSED SUBJECT MATTER

1. Field of the Disclosed Subject Matter

The disclosed subject matter relates to catheters for treating luminal systems of a patient. Specifically, the disclosed subject matter relates to a monolithic elongate tubular shaft member having an inner core made of a first material and an outer layer made of a second material, the inner core having a first lumen and a second lumen defined therein with substantially uniform cross-sections, respectively.

2. Description of Related Subject Matter

Balloon catheters are used for a wide range of treatments in the medical field. For example, balloon catheters are used for percutaneous transluminal coronary angioplasty (PTCA) and for the delivery of stents or the like.

In percutaneous transluminal coronary angioplasty (PTCA) procedures, a guiding catheter is advanced in the vasculature of a patient until the distal tip of the guiding catheter is seated in the ostium of a desired coronary artery. A guidewire is advanced out of the distal end of the guiding catheter into the coronary artery until the distal end of the guidewire crosses a lesion to be dilated. A dilatation catheter, having an inflatable balloon on the distal portion thereof, is advanced into the coronary anatomy over the previously introduced guidewire until the balloon of the dilatation catheter is positioned across the lesion. Once positioned, the dilatation balloon is inflated with inflation fluid one or more times to a predetermined size at a suitable pressure to compress the stenosis against the arterial wall to open up the vascular passageway. Generally, the inflated diameter of the balloon is approximately the same diameter as the native diameter of the body lumen being dilated to complete the dilatation but not over expand the artery wall. After the balloon is deflated, blood resumes through the dilated artery and the dilatation catheter and the guidewire can be removed there from.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians may additionally or alternatively implant an intravascular prosthesis inside the artery at the site of the lesion. Such stents may be bare metal, polymeric, or coated with a drug or other therapeutic agent. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter with the stent implanted within the artery at the site of the dilated lesion. Coverings on an inner or an outer surface of the stent have been used in, for example, the treatment of pseudoaneurysms and perforated arteries, and to prevent prolapse of plaque. Similarly, vascular grafts comprising cylindrical tubes made from tissue or synthetic materials such as polyester, expanded polytetrafluoroethylene, and DACRON may be implanted in vessels to strengthen or repair the vessel, or used in an anastomosis procedure to connect vessels segments together. For details of example stents, see for example, U.S. Pat. No. 5,507,768 (Lau, et al.) and U.S. Pat. No. 5,458,615 (Klemm, et al.), which are incorporated herein by reference.

In addition to PTA, PTCA, and atherectomy procedures, balloon catheters are also used to the peripheral system such as in the veins system or the like. For instance, a balloon catheter is initially advanced over a guidewire to position the balloon adjacent a stenotic lesion. Once in place, the balloon is then inflated, and the restriction of the vessel is opened. Likewise, balloon catheters are also used for treatment of other luminal systems throughout the body.

Typically, balloon catheters comprise a hollow catheter shaft with a balloon secured at a distal end. The interior of the balloon is in a fluid flow relation with an inflation lumen extending along a length of the shaft. Fluid under pressure can thereby be supplied to the interior of the balloon through the inflation lumen. To position the balloon at the stenosed region, the catheter shaft is designed to have suitable pushability (i.e., ability to transmit force along the length of the catheter), trackability, and flexibility, to be readily advanceable within the tortuous anatomy of the vasculature. Conventional balloon catheters for intravascular procedures, such as angioplasty and stent delivery, frequently have a relatively stiff proximal shaft section to facilitate advancement of the catheter within the body lumen and a relatively flexible distal shaft section to facilitate passage through tortuous anatomy, such as distal coronary and neurological arteries, without damage to the vessel wall.

Traditional catheter shafts are often constructed with inner and outer member tubing separately with an annular space therebetween for balloon inflation. In the design of catheter shafts, it is desirable to predetermine or control characteristics such as strength, stiffness and flexibility of various sections of the catheter shaft to provide the desired catheter performance. This is conventionally performed by combining separate lengths of tubular members of different material and/or dimensions and then assembling the separate members into a single shaft length. However, the transition between sections of different stiffness or material can be a cause of undesirable kinking along the length of the catheter. Such kinking is particularly evident in rapid exchange (RX) catheters, wherein the proximal shaft section does not include the additional structure of a guidewire lumen tube. For example, a conventional RX catheter generally consists at its proximal end of a hypotube having a single inflation lumen therethrough and at its distal end, a dual lumen or coaxial tube configuration having both a guidewire lumen and an inflation lumen therein. Known techniques to minimize kinking at the transition between the more rigid proximal section and the more flexible distal section include bonding two or more segments of different flexibility together to form the shaft. Such transition bonds need to be sufficiently strong to withstand the pulling and pushing forces on the shaft during use.

To address the described issues, catheters having varied flexibility and/or stiffness have been developed. For example, each of U.S. Pat. No. 4,782,834 to Maguire and U.S. Pat. No. 5,370,655 to Burns discloses a catheter having sections along its length which are formed from materials having a different stiffness; U.S. Pat. No. 4,976,690 to Solar discloses a catheter having an intermediate waist portion which provides increased flexibility along the catheter shaft; U.S. Pat. No. 5,423,754 to Cornelius discloses a catheter having a greater flexibility at its distal portion due to both a material and dimensional transition in the shaft; U.S. Pat. No. 5,649,909 to Cornelius discloses a catheter having a proximal portion with greater stiffness due to the application of a polymeric coating thereto; and U.S. Publication No. 2010/0130925 to Haslinger discloses a multilayer catheter shaft using a combination of a high Shore D durometer value material and a lower Shore D durometer value material to reduce kinking.

However, there remains a need for a catheter shaft with an improved combination of characteristics such as strength, flexibility and ease of manufacture.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve the above and other advantages and in accordance with the purpose of the disclosed subject matter, as embodied and broadly described, the disclosed subject matter includes, according to one embodiment, a multi-lumen catheter comprising a monolithic elongate tubular shaft member having a proximal end, a distal end and a longitudinal length therebetween, wherein the tubular shaft member has an outer cross-sectional dimension that varies along the length of the tubular shaft member. The tubular shaft member has an inner core made of a first material and an outer layer made of a second material, wherein the inner core has a first lumen and a second lumen defined therein. The first lumen has a first lumen cross-section and a length extending at least along a portion of the length of the tubular shaft member, the first lumen cross-section being substantially uniform along the length of the first lumen, and the second lumen has a second lumen cross-section and a length extending along the length of tubular shaft member, the second lumen cross-section being substantially uniform along the length of the second lumen.

According to a further aspect of the disclosed subject matter, a method of forming a multi-lumen catheter is provided comprising extruding a first material to form an inner core with a first lumen and a second lumen defined therein, the first lumen having a first lumen cross-section and the second lumen having a second lumen cross-section; and extruding a second material generally surrounding the inner core to form an extrudate having an outer layer of the second material surrounding the inner core of the first material, the extrudate having an outer cross-sectional dimension. The method further includes internally pressurizing the first lumen and the second lumen, respectively, while drawing a length of the extrudate at a varied speed to vary the outer cross-sectional dimension along the length thereof; and cooling the extrudate to form a monolithic elongate tubular shaft member having a proximal end, a distal end and a longitudinal length therebetween, the tubular shaft member having an outer cross-sectional dimension that varies along the length of the tubular shaft member.

It is to be understood that both the foregoing general description and the following detailed description are embodiments and are intended to provide further explanation of the disclosed subject matter claimed. The accompanying drawings, which are incorporated in and constitute part of this specification, are included to illustrate and provide a further understanding of the system and method of the disclosed subject matter. Together with the description, the drawings serve to explain the principles of the disclosed subject matter.

BRIEF DESCRIPTION OF THE DRAWINGS

The subject matter of the application will be more readily understood from the following detailed description when read in conjunction with the accompanying drawings, in which:

FIG. 1 is a schematic side view of a representative embodiment of a multi-lumen catheter with an over-the-wire configuration, according to an embodiment of the disclosed subject matter;

FIG. 3 is an enlarged cross-section side view of the multi-lumen catheter at 3-3 of FIG. 2, according to the disclosed subject matter;

FIGS. 4 and 5 are schematic side views of a tubular shaft member for an over-the-wire catheter and a rapid exchange catheter, respectively, according to embodiments of the disclosed subject matter;

FIG. 6 is a cross-section end view of the tubular shaft member at 6-6 of FIG. 4, according to an embodiment of the disclosed subject matter;

FIG. 7 is a cross-section end view of the tubular shaft member at 7-7 of FIG. 4, according to an embodiment of the disclosed subject matter;

FIG. 8 is a cross-section end view of the tubular shaft member at 8-8 of FIG. 4, according to an embodiment of the disclosed subject matter;

DETAILED DESCRIPTION

Figure 2B:
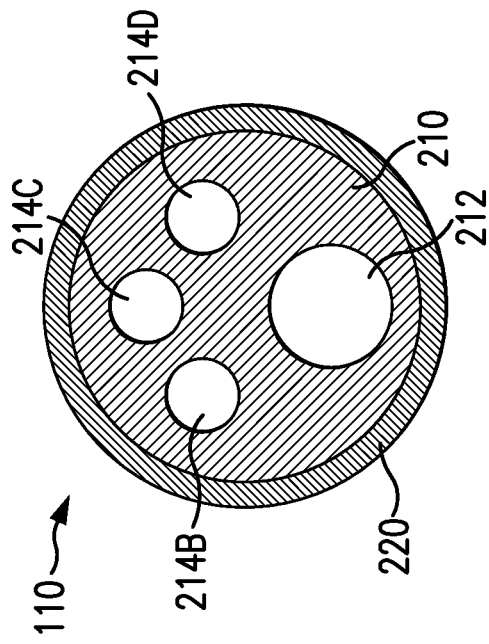
FIG. 2B is a cross-section of a multi-lumen catheter, according to another embodiment of the disclosed subject matter.

Reference will now be made in detail to embodiments of the disclosed subject matter, an example of which is illustrated in the accompanying drawings. The examples are not intended to limit the scope of the disclosed subject matter in any manner. The disclosed subject matter will be described in conjunction with the detailed description of the system.

As disclosed herein, the devices presented herein can be used for treating a luminal system of a patient. In particular, the disclosed subject matter is particularly suited for treatment of the cardiovascular system of a patient, such as delivery of a medical device into the vasculature.

In accordance with an aspect of the disclosed subject matter, a multi-lumen catheter is provided. To achieve the above and other advantages and in accordance with the purpose of the disclosed subject matter, as embodied and broadly described, the disclosed subject matter includes, according to one embodiment, a multi-lumen catheter comprising a monolithic elongate tubular shaft member having a proximal end, a distal end and a longitudinal length therebetween, wherein the tubular shaft member has an outer cross-sectional dimension that varies along the length of the tubular shaft member. The tubular shaft member has an inner core made of a first material and an outer layer made of a second material, wherein the inner core has a first lumen and a second lumen defined therein. The first lumen has a first lumen cross-section and a length extending at least along a portion of the length of the tubular shaft member, the first lumen cross-section being substantially uniform along the length of the first lumen, and the second lumen has a second lumen cross-section and a length extending along the length of tubular shaft member, the second lumen cross-section being substantially uniform along the length of the second lumen.

According to a further aspect of the disclosed subject matter, a method of forming a multi-lumen catheter is provided comprising extruding a first material to form an inner core with a first lumen and a second lumen defined therein, the first lumen having a first lumen cross-section and the second lumen having a second lumen cross-section; and extruding a second material generally surrounding the inner core to form an extrudate having an outer layer of the second material surrounding the inner core of the first material, the extrudate having an outer cross-sectional dimension. The method further includes internally pressurizing the first lumen and the second lumen, respectively, while drawing a length of the extrudate at a varied speed to vary the outer cross-sectional dimension along the length thereof; and cooling the extrudate to form a monolithic elongate tubular shaft member having a proximal end, a distal end and a longitudinal length therebetween, the tubular shaft member having an outer cross-sectional dimension that varies along the length of the tubular shaft member.

For purpose of illustration and not limitation, reference will now be made in detail to specific embodiments, examples of which are illustrated in the accompanying drawings. For the purposes of this disclosure, like reference numbers in the figures shall refer to like features unless otherwise indicated.

Solely for purpose of illustration, an exemplary embodiment of a multi-lumen catheter 100 is shown in FIG. 1. The multi-lumen catheter 100 includes a monolithic elongate tubular shaft member 110 having a proximal end, a distal end and a longitudinal length therebetween. The tubular shaft member 110, being a monolithic elongate member, can exhibit various beneficial characteristics not achieved by multi-piece constructions, such as improved pushability, reduced profile, increased flexibility, and 1 to 1 torque ratio along the length of the catheter 100.

The tubular shaft member 110 can be made of a variety of suitable configurations. For example, the shaft can provide an over the wire (OTW) configuration with a guidewire lumen extending generally across the entire length of the shaft. As an alternative embodiment, the shaft of the catheter can be a rapid exchange (RX) configuration with a guidewire lumen extending distally from a proximal guidewire port to or near the distal end of the shaft, as known in the art.

For purpose of illustration and not limitation, FIG. 1 depicts an OTW configuration for a balloon catheter and includes a balloon member 120 coupled to the tubular shaft member 110 proximate the distal end thereof. An adaptor 150 is positioned at the proximal end of the tubular shaft member 110 and is further discussed herein. As illustrated herein, a system guidewire 125 is also depicted extending the length of the tubular shaft member 110 through the balloon member 120 and ends at a distal tip 126. The distal tip 126 of the guidewire 125 is disposed distal to the balloon member 120, as shown. Although FIG. 1 depicts a balloon catheter, any of a variety of other types of catheters, including delivery systems, can be used in accordance with the disclosed subject matter.

In accordance with one aspect of the disclosed subject matter, the monolithic tubular shaft member 110 includes a plurality of materials. For example, and as embodied herein, the tubular shaft member 110 includes an inner core made of a first material and an outer layer made of a second material. FIG. 2 represents a cross-section of the multi-lumen catheter 100 at 2-2 of FIG. 1. As depicted in FIG. 2, the tubular shaft member 110 includes the inner core 210 made of the first material and the outer layer 220 made of the second material. The first and second materials are selected for desired characteristics, such as but not limited to pushability, torque, and flexibility.

As shown in the embodiment of FIG. 2, the inner core 210 has a first lumen 212 and a second lumen 214 defined therein. For example, the first lumen 212 can define the guidewire lumen. Since the catheter 100 of FIG. 1 and FIG. 2 is of the OTW configuration, the guidewire lumen 212 extends generally across the entire length of the tubular shaft member 110. As depicted in FIG. 1, a guidewire 125 therefore can extend within the first lumen 212 the length of the catheter 100. As shown in FIG. 1, the guidewire 125 is depicted extending beyond the distal end of the catheter. The first lumen 212 includes a first proximal port and a first distal port, as further discussed herein. Although depicted with only two lumens, additional lumens also can be defined in the inner core and/or the outer layer if desired in accordance with the discussed subject matter.

The first lumen 212 can have any suitable cross-sectional shape, including elliptical, polygon, or prismatic, although a circular cross-section is depicted herein. The first lumen 212 can also have any suitable size and diameter depending upon the desired application. The catheter 100 is suitably sized and configured for delivery within a corresponding body lumen for the intended indication, such as a vasculature for vascular intervention. In the embodiment of FIG. 2, the first lumen 212 has a substantially circular cross-section and is configured to receive the guidewire therethrough. The cross-section of the first lumen 212 is substantially uniform in size and shape along the length of the first lumen 212. Thus, the diameter of the first lumen 212 remains substantially uniform along its length. The diameter of the first lumen 212 can be any suitable dimension such as, for example, 0.0170 inches when used for a 0.014 inch guidewire. The diameter of the first lumen 212 can range from approximately 0.015 to approximately 0.021 inches.

The second lumen 214 can define a fluid lumen, such as an inflation lumen for a balloon. In this manner, the second lumen or fluid lumen 214 is in fluid communication with an inner chamber 122 of the balloon member 120, as described further below. The second lumen 214 defines a pathway for fluid or an inflation medium to be introduced through the tubular shaft member 110. Fluid can be introduced into the second lumen 214 at a proximal end of the catheter 100 via a luer adaptor or the like, as further discussed herein. The second lumen 214 can supply an inflation medium under positive pressure and can withdraw the inflation medium, e.g., by negative pressure, from the balloon member 120. The balloon member can thus be inflated and deflated via the second lumen 214, as further discussed below. Additional or alternative uses for the second lumen include fluid supply lumen for infusion or needle catheters, or for fluid flow lumens such as for perfusion or aspiration catheters.

Figure 2A:
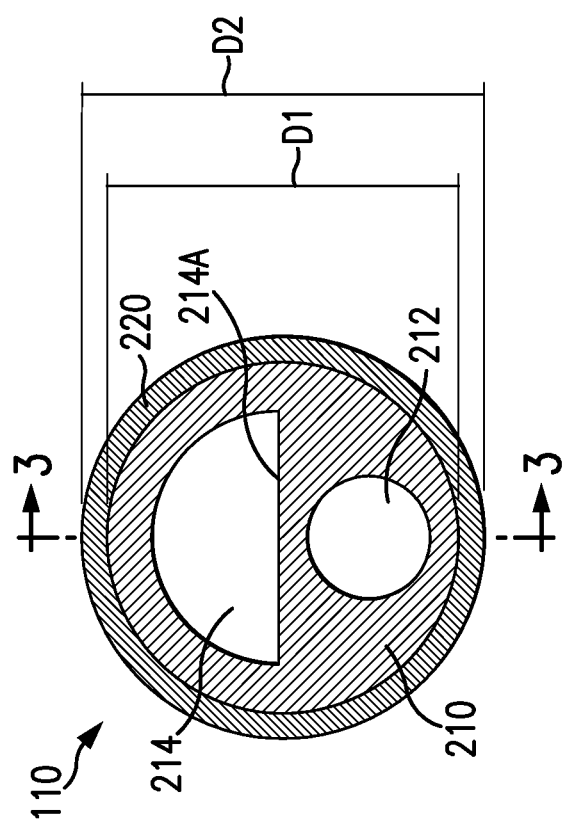
FIG. 2A is a cross-section of the multi-lumen catheter at 2-2 of FIG. 1, according to an embodiment of the disclosed subject matter.

The second lumen 214 can also have any suitable cross-sectional shape, including elliptical, polygon, or prismatic. The second lumen 214 can also have any suitable size and diameter depending upon the desired application. In accordance with another aspect of the disclosed subject matter however, the second lumen can include at least one of a semi-circular cross-section or a circular cross-section. For example, and as depicted in the embodiment of FIG. 2A, the second lumen 214 has a substantially semi-circular cross-section and is configured to receive inflation medium therethrough. The second lumen 214 is positioned adjacent the first lumen 212 such that the substantially straight edge 214A of the semicircle is proximate the first lumen 212. When inflation medium is received in the second lumen 214, the geometry of the second lumen 214 facilitates a generally uniform force distribution across the substantially straight edge 214A caused by the inflation medium pressure. Unlike a conventional "smiley" configuration, the relationship of the substantially straight edge relative the first lumen prevents or minimizes an expansion of the core material toward the first lumen. Hence, pressurization of the second lumen will reduce the likelihood of collapse of the first lumen or of "locking" of the guidewire positioned therein. Hence, the configuration of the semi-circular cross-section of the second lumen relative the first lumen assists to maintain the integrity of the inner core 210 so that the pressurization does not cause the collapse of the first lumen 212. In another representative embodiment, the second lumen 214 comprises a plurality of individual inflation lumens 214B-214D, as depicted in FIG. 2B. The plurality of individual inflation lumens can be configured independent and isolated from each other, or can be in fluid communication with each other.

The cross-section of the second lumen 214 is substantially uniform in size and shape along the length of the second lumen 214. The cross-dimension of the second lumen 214 can be any suitable dimension such as, for example, approximately 0.012 inches when configured as a single semi-circular cross-section for inflation of a coronary balloon.

The inner core 210 can have any suitable cross-sectional shape, including elliptical, polygon, or prismatic, although a circular cross-section is depicted herein. The inner core 210 can also have any suitable size and diameter depending upon the desired application. As depicted in FIG. 2A, the inner core 210 has an outer cross-sectional dimension D1. For example, for a PCTA balloon catheter the cross-sectional dimension D1 can range from approximately 0.02 inches to approximately 0.05 inches, and in particular be approximately 0.0358 inches at the distal end. As previously noted, and in accordance with the disclosed subject matter, at least a portion of the length of the shaft member varies in cross-sectional dimension. Similarly, the outer cross-sectional dimension D1 of the inner core is not constant along the length of the tubular shaft member 110. For example, and as depicted in FIG. 2A, the outer cross-sectional dimension D1 of the inner core varies along the length of the tubular shaft member from the proximal end of the catheter 100 to the distal end of the catheter 100. Although the outer cross-sectional dimension D1 varies in dimension, the dimensions of the first lumen 212 and the second lumen 214 are substantially uniform along the length of the tubular shaft member from the proximal end of the catheter 100 to the distal end of the catheter 100.

In accordance with the discussed subject matter, and as embodied herein, the tubular shaft member 110 further includes an outer layer 220 made of a second material. The outer layer 220 generally surrounds the inner core 210 is made of a different material than the first material, as further discussed herein. Similar to the inner core, the outer layer can have any suitable cross-sectional shape, including elliptical, polygon, or prismatic, or a circular cross-section as depicted. Generally, the inner core 210 and the outer layer 220 can have similar cross-sectional shape. The outer layer 220 and the inner core 220 together can also have any suitable size and diameter depending upon the desired application.

As depicted in FIG. 2A, the tubular shaft member 110 has an outer cross-sectional dimension D2. For example, a PCTA catheter as embodied herein can have cross-sectional dimension D2 ranging from approximately 0.03 to approximately 0.05 inches. The outer cross-sectional dimension D2 of the tubular shaft member 110 varies along the length of the tubular shaft member from the proximal end of the catheter 100 to the distal end of the catheter 100. That is, the cross-sectional dimension of the outer surface is not consistent along at least a portion of the length of the tubular member. Although the outer cross-sectional dimension D2 varies in dimension, the dimensions of the first lumen 212 and the second lumen 214 are substantially uniform along the length of the tubular shaft member from the proximal end of the catheter 100 to the distal end of the catheter 100. In one embodiment, the outer cross-sectional dimension D2 and the outer cross-sectional dimension D1 can vary proportionally to each other along the length of the tubular shaft member and can vary uniformly along at least a portion of the tubular shaft member 110. In another embodiment, the outer cross-sectional dimension D2 and the outer cross-sectional dimension D1 each vary independently.

In an alternate embodiment, the outer cross-sectional dimension D2 can remain substantially uniform along the length of the tubular shaft member 110 whereas the outer cross-sectional dimension D1 varies along the length of the tubular shaft member 110. In such embodiment, the inner core 210 decreases in cross-sectional dimension whereas the outer layer 210 remains substantially uniform. For example, the inner core can be made according to the method describe in further details below, and the outer layer can be applied after the inner core is made with the varied outer cross-sectional dimensions.

FIG. 3 represents a cross-section of the tubular shaft member 110 at 3-3 of FIG. 2A. As depicted in FIG. 2A, the inner core 210 and the outer layer 220 together vary in outer cross-sectional dimension. In the embodiment of FIG. 3, for purpose of illustration and not limitation the inner core 210 and the outer layer 220 vary proportionally with each other. As depicted in the representative embodiment of FIG. 3, the first lumen 212 and the second lumen 214 are substantially uniform in cross-sectional dimension. For purpose of example in this embodiment, the cross-sectional dimension of the tubular shaft member 110 is generally constant along a proximal section and along a distal section, with a taper or decreasing cross-sectional dimension along an intermediate section. In one example for a catheter approximately 185 cm in length, the intermediate section can be approximately 25.5 cm in length with the proximal section having approximately 0.052 inch outer diameter and the distal section having approximately 0.036 inch outer diameter. In addition thereto, the intermediate section can range from approximately 2 cm (0.7874 inches) to approximately 185 cm (72.83 inches), the outer diameter in the proximal portion can range from approximately 0.03 inches to approximately 0.08 inches, and the outer diameter in the distal section can range from approximately 0.02 inches to approximately 0.05 inches.

The slope or angle of the taper in the intermediate section can depend upon the desired needs. In one embodiment, the intermediate section has a slope of approximately 0.15. The slope can vary and range from approximately 0.0004 to approximately 0.381. Furthermore, the tubular shaft member 110 can have a continuous or uniform taper or the taper can vary in slope along the length thereon, such as parabolicly. Additionally, and as previously noted, the change in cross-sectional dimension can be provided along only a portion of the tubular shaft or can extend the entire length of the shaft portion.

FIG. 4 and FIG. 5 represent partial cross-sectional views of the tubular shaft member 110 in the OTW configuration and the RX configuration, respectively. FIGS. 4 and 5 depict the proximal section P, a distal section D, and an intermediate section M disposed between the proximal section P and the distal section D. In FIG. 5, a proximal guidewire port 155 is provided in the intermediate section M, which is further discussed herein. In the embodiments of FIGS. 4 and 5, the outer cross-sectional dimensions of the inner core 210 and the outer layer 220 vary independently to each other, as further discussed with respect to FIG. 6, FIG. 7, and FIG. 8.

FIG. 6 represents a cross-section of the tubular shaft member 110 at 6-6 of FIG. 4 in the proximal section P. The outer cross-sectional dimension D2 of the tubular shaft member 110 at the proximal section P is at a maximum dimension. Likewise, the outer cross-sectional dimension D1 of the inner core 210 is at a maximum dimension. Accordingly, the catheter 100 has embodied herein maximum profile in the proximal section P.

FIG. 7 represents a cross-section of the tubular shaft member 110 at 7-7 of FIG. 4 in the intermediate section M. The tubular member 110 tapers in the intermediate section M such that the outer cross-sectional dimension D2 of the tubular shaft member 110 and the outer cross-sectional dimension D1 of the inner core 220 vary. However, as depicted in FIG. 6 and FIG. 7, the cross-sectional dimensions of the first lumen 212 and the second lumen 214 are substantially uniform within acceptable tolerances.

FIG. 8 represents a cross-section of the tubular shaft member 110 at 8-8 of FIG. 4 in the distal section D. The outer cross-sectional dimension D2 of the tubular shaft member 110 embodied herein at the distal section D is at a minimum dimension. Likewise, the outer cross-sectional dimension D1 of the inner core 210 is at a minimum dimension. However, as depicted in FIG. 6-FIG. 8, the cross-sectional dimensions of the first lumen 212 and the second lumen 214 are substantially uniform. The catheter 100 has its smallest profile in the distal section D. Therefore, the outer cross-sectional dimension D2 of the tubular shaft member 110 decreases distally along the tubular shaft member 110. The spacing distance between the first lumen 212 and the second lumen 214 can decrease from the proximal section P to the distal section D or can remain substantially uniform, as depicted in FIG. 6-8 with respect to X1-X3.

Figure 9:
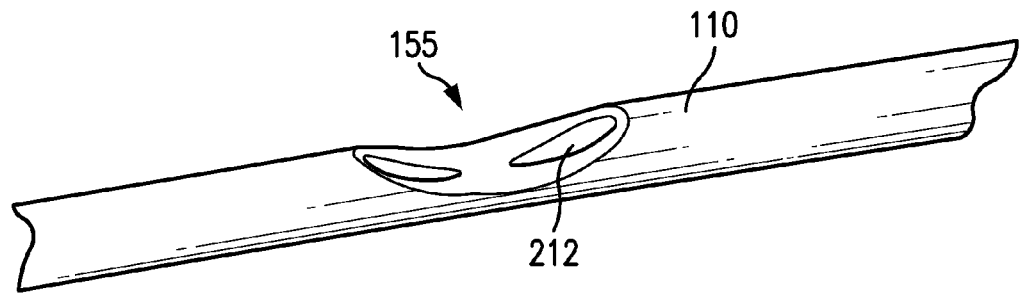
FIG. 9 is an enlarged perspective view of a notch for a guidewire port for a rapid exchange catheter shaft, according to an embodiment of the disclosed subject matter.

FIG. 9 represents a detailed view of a representative embodiment of the proximal guidewire port 155 of FIG. 5 for a catheter of RX configuration. The proximal guidewire port 155 is spaced distally from the proximal end of the tubular shaft member. The proximal guidewire port 155 is defined through the external surface of the tubular shaft member 110 and is fluidly coupled with the first lumen 212. In the embodiment of FIGS. 5 and 9, the proximal guidewire port 155 is embodied as a notch. The proximal guidewire port 155 or notch extends through the outer layer and into the inner core 210 to intersect the first lumen 212. The notch can be formed with any of a variety of shapes or configurations, and can be made using connection process, such as mechanical cutting, milling or laser. The proximal guidewire port 155 allows the guidewire to exit the first lumen 212 at this location.

For a catheter of the OTW configuration, the proximal guidewire port 155 is generally located at the proximal end of the catheter. FIG. 1 depicts catheter 100 of the OTW configuration with the proximal guidewire port 155 proximate to the tubular shaft member 110.

Figure 10:
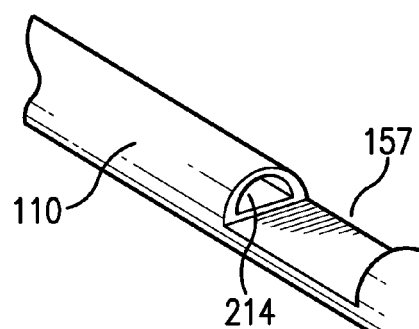
FIG. 10 is an enlarged perspective view of a proximal end of a tubular shaft member, according to an embodiment of the disclosed subject matter.

In either OTW or RX configuration, a proximal fluid port is fluidly coupled with the second lumen 214. FIG. 10 represents the tubular shaft member 110 at a proximal end depicting the proximal fluid port 157. The proximal fluid port embodied herein as defined through the extension surface of the tubular shaft as a notch extending through the outer layer and into the inner core to the second lumen 214. The proximal fluid port can be formed with a variety of shapes and using any conventional process. The proximal fluid port 157 receives an inflation medium or pressurized fluid and facilitates the channeling of the inflation medium into the second lumen 214. In this embodiment, the proximal end of the second lumen 214 proximal to the proximal fluid port 157 includes a plug 112 to prevent the inflation medium from exiting proximally. The proximal guidewire port 155 is also depicted in FIG. 10. In FIG. 10, the adaptor is not depicted, but is further discussed herein.

Figure 11:
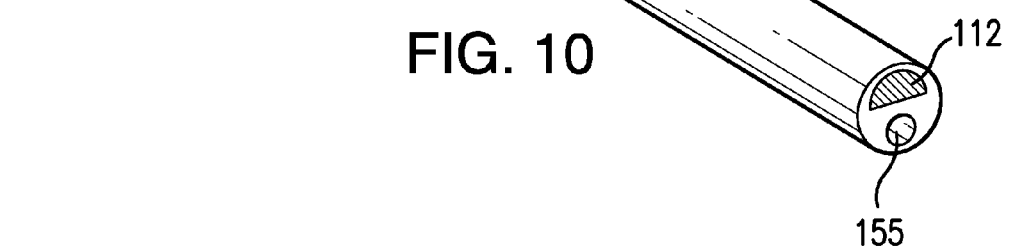
FIG. 11 is an enlarged perspective view in cross-section of a manifold coupled to a tubular shaft member for an over-the-wire catheter, according to an embodiment of the disclosed subject matter.

FIG. 11 represents a partial cross-sectional view of the proximal end of the catheter 100 of FIG. 1. An adaptor 150 or manifold can be provided at the proximal end of the catheter for access to the proximal fluid port 157 and, if desired, the proximal guidewire port 155. As depicted for the OTW configuration in FIG. 11, the manifold has a Y-shape with a luer connector at the proximal end of one branch 151 to receive the fluid source, and a separate hemostatic valve on another branch 153 to receive the guidewire. A conventional device, such as but not limited to an indeflator or a syringe, can be connected to the luer connector to introduce the fluid to the fluid lumen. A locking mechanism can further be provided to lock the operating position of the indeflator or syringe. For a RX configuration, the manifold need only comprise a single branch for introducing an inflation medium into the second lumen 214 via the proximal fluid port 157.

The indeflator or other fluid source can be configured to control the inflation and deflation of the balloon member, as further discussed herein. A pressure gauge can be provided with the indeflator to monitor and/or maintain the pressure system of the catheter. The indeflator likewise can allow for the rapid release of pressure. The indeflator can have a locking mechanism to maintain negative pressure in the catheter, which can decrease the profile of the catheter.

Figure 12:
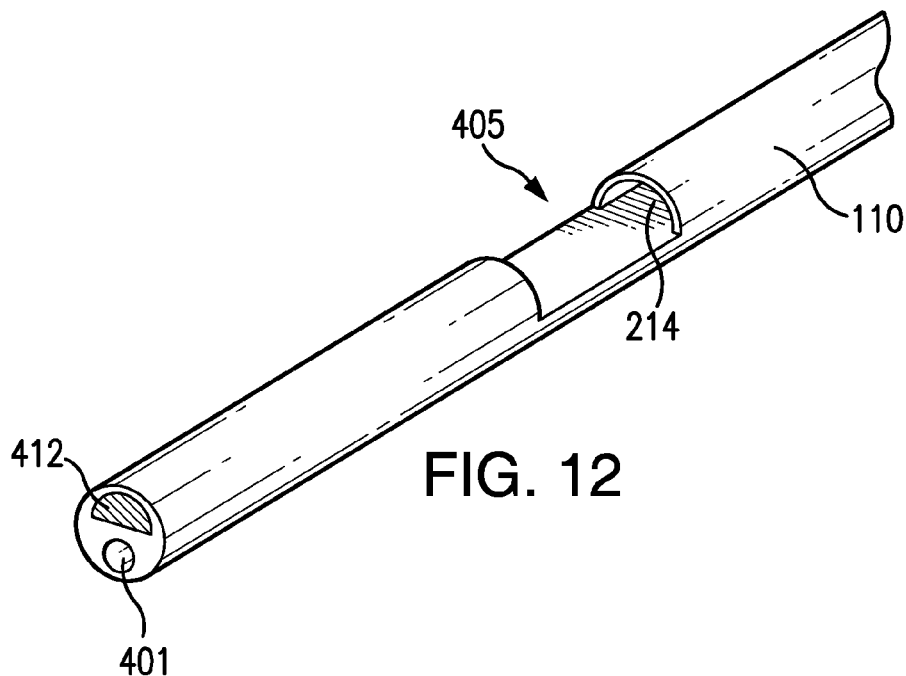
FIG. 12 is an enlarged perspective view of distal end of a tubular shaft member, according to an embodiment of the disclosed subject matter.

FIG. 12 represents the distal end of the tubular shaft member 110 and depicts both a distal guidewire port 401 and a distal flow port 405. The distal guidewire port 401 is fluidly coupled with the first lumen 212 to allow access for the guidewire 125 within the first lumen 212. As further depicted in FIG. 1, the distal tip 126 of the guidewire 125 is distal to the distal guidewire port 401 in this FIG.

Turning back to FIG. 12, the distal flow port 405 is fluidly coupled with the second lumen 214. The distal flow port 405 defines an opening within the second lumen 214 to allow inflation medium to exit the second lumen 214. In one embodiment, the distal flow port 405 is defined by a notch extending through the outer layer and into the inner core to intersect the second lumen 214. Distally of the distal flow port 405, the second lumen 214 is sealed, such as by a plug 412 to prevent the flow of inflation medium distal to the distal end of the tubular shaft member 110. The distal flow port 405 is disposed within an inner chamber 122 of the balloon member 120 and is spaced proximally from the distal end of the tubular shaft member, as further described herein. The second lumen 214 facilitates the inflation and deflation of the balloon member 120 via the distal flow port 405.

Figure 13:
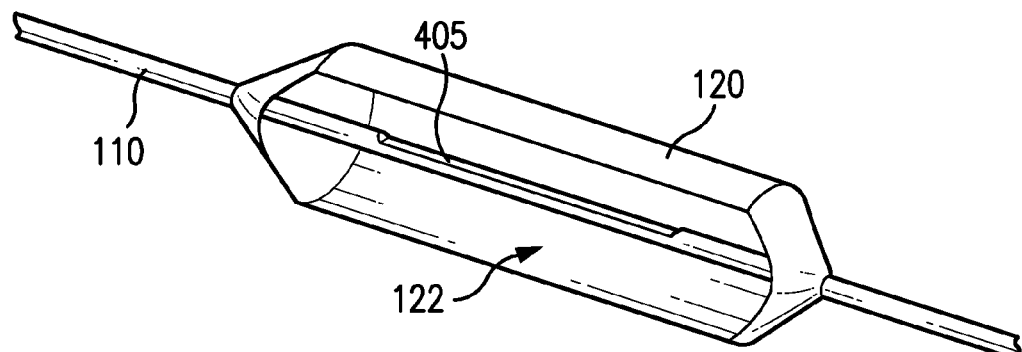
FIG. 13 is an enlarged perspective view of a partial cross-section of an inflated balloon coupled to a tubular shaft member, according to an embodiment of the disclosed subject matter.

FIG. 13 depicts a partial cross-sectional view of the balloon member 120 coupled to the distal end portion of the tubular shaft member 110. The balloon member 120 has an exterior surface and an interior surface. The interior surface of the balloon member 120 defines an inner chamber 122 with an interior volume. The inner chamber 122 is in fluid communication with the second lumen 214 of the tubular shaft member 110 via the distal flow port 405. The tubular shaft member 110 extends through the balloon member 120. FIG. 13 shows the tubular shaft member 110 extending the entire length of the balloon member 120, although the tubular shaft member 110 can terminate and transition into a single lumen member within or proximal to the inner chamber 122, if needed or desired. As embodied herein, the distal flow port 405 can be defined along the tubular shaft member 110 along the working length of the balloon member 120 to ensure inflation medium reaches with the inner chamber 122 of the balloon member 120.

The balloon member 120 is transitionable between a deflated configuration and an inflated configuration. The balloon member 120 is depicted in an inflated condition in the drawing of FIG. 13. The balloon member 120 has an overall length with a working length extending at least a portion of the overall length. At least a portion of the exterior surface of the balloon member 120 along the working length is configured to engage a body lumen of a patient when the balloon member 120 is in the inflated configuration.

In another embodiment, the balloon member 120 can have a drug coating on the balloon to deliver the drug to the lesion site. Additionally, or alternatively, a stent can be mounted on an exterior surface of the balloon member 120. Examples of various known catheters and stents are disclosed in U.S. Pat. Nos. 5,649,977; 5,464,650; 5,591,227, 7,378,105; 7,445,792; 7,335,227, each of which is hereby incorporated by reference in its entirety. Examples of other balloon and catheter embodiments the features of which can be employed in accordance with the disclosed subject matter include, for purpose of illustration and not limitation, U.S. Pat. Nos. 4,748,982; 5,496,346; 5,626,600; 5,300,085, 6,406,457 and U.S. application Ser. Nos. 12/371,426; 11/539,944; 12/371,422, each of which is hereby incorporated by reference in its entirety.

The tubular shaft member 110 can further include a tip 140 at the distal end of the catheter 100, as illustrated in FIG. 1. The tip 140 can be monolithic with the tubular member 110 and formed by same materials previously discussed with respect to the tubular member 110. Additionally or alternatively, the distal tip can be formed at least in part by the distal leg of the balloon member. In alternate embodiments, the tip can be formed as separate member, such as from a relatively soft material, which can be softer than the tubular shaft member 100 to reduce trauma to the vasculature of a patient. According to one embodiment, the tip can be molded from a polyether block amide (PEBAX) such as PEBAX 4033. It is further contemplated that the tip 140 may be made of a material that is harder and/or has greater stiffness than the tubular shaft member 110.

The tip 140 can also include a radiopaque material or have a radiopaque coating. United States Publication Number 2011/0070355 to Bavaro et al. and U.S. Pat. Nos. 7,303,798 to Bavaro et al., 7,322,959 to Warnack at al., and 7,833,597 to Bavaro et al. discuss further examples of radiopaque materials and the disclosures of which are herein incorporated by reference in their entirety. Various other materials that are suitable with the catheter shaft material can be used for the tip as is known in the art.

According to another aspect of the disclosed subject matter, the inner core and the outer layer are extruded together to form the tubular shaft member. The inner core can comprise a first material of suitable strength, flexibility, and desired characteristics. The first material of the inner core can include at least one of Nylon, Nylon 12, Nylon TR55, transparent amorphous nylon, and high density polyethylene (HDPE). Further, the first material of the inner core can be a lubricious material to reduce friction such as guidewire passing through the first lumen, Examples of lubricious material include such as HDPE, UHMWPE, PTFE, polyolefin blends of PEO's such as poly(ethylene oxide), polyvinylpyrrolidone (PVP), Polydimethyl acrylamide, polyvinylalcohol (PVA), and other suitable materials.

The outer layer can be coextruded with or extruded subsequently over the inner core. As embodied herein, the outer layer can comprise a second material that is different than the first material of the inner core. The second material can comprise a suitable strength, flexibility, and desired characteristics. Additionally or alternatively, the second material can exhibit chemical resistance or chemical inaction. Further, the second material can be of suitable material to facilitate anti-kinking and/or reduce kinking such as that would otherwise occur with the first material alone. For example, the second material can comprise at least one of Pebax 63D, Pebax 70D, and Pebax 72D.

In further embodiments, the second material can comprise at least one of an amorphous polyamide selected from polyamide such as EMS TR 55 (transparent amorphous nylon 12), Arkema Rilsan G110 (transparent amorphous nylon 12), Cristamid MS 110 (transparent amorphous nylon 12), polyamide 11, polyamide 6, or polyamide 6,6. This polyamide is preferably a copolyamide comprising cycloaliphatic, and/or aromatic, and/or aliphatic segment, and/or PEBAX. In another embodiment, the outer layer is blended with a softer polyamide such as a crystalline or semi-crystalline copolymer of nylon 12 and polytetramethylene oxide or polytetramethylene glycol, e.g. Pebax 72D or Pebax 70D or PET or polyester elastomer such as Hytrel for example, or polyester such as Melinar for example, or polyurethane such as Pellethane for example, or polyvinylidene fluoride such as Kynar for example. This blending offers a higher strength outer layer for greater pushability and resistance to collapse, while the copolymer operates to resist kinking and yield greater flexibility. Although various blends of high miscibility can be used, blend ratios are such that the lower durometer polymer forms a virtual continuous phase and the high durometer polymer forms a virtual reinforcement. Other materials are also contemplated for the inner core, when the outer layer has a glass transition or melting temperature that can be lower than, or at least approximately equal to, the surface temperature of the mold during the blowing or forming process of the balloon member, as further discussed herein.

In accordance with another aspect, an intermediate layer or material can be disposed between the inner core and the outer layer. For example, the intermediate layer can be a tie or bonding layer to join the inner core and the outer layer. The intermediate layer can comprise at least one of Primacore, PET, Polyester Elastomer, high density polyethylene, and Pebax or other soft copolyamide, depending on the material of the inner core and outer layer as known in the art.

In another embodiment, a liner can be provided along at least a portion of the length of the lumen used as a guidewire lumen, such as the first lumen 212 as embodied herein. The liner can be coextruded with the first material and the second material. The liner can furthermore exhibit a suitable strength, flexibility, and desired characteristics, such as for example, chemical resistance or chemical inaction. The liner can comprise at least one of HDPE, FEP, and Pebax 72D.

The outer layer can further include an exterior coating of suitable material along all or a portion of its length. The coating can be a lubricious material and can further enhance chemical resistance and anti-kinking of the catheter. The outer layer can be further coated with any of a variety of materials and techniques to enhance performance if desired, including a number suitable coatings and coating techniques subject to patent matters owned by Abbott Laboratories such as U.S. Pat. No. 6,541,116, U.S. Pat. No. 6,287,285, and U.S. Pat. No. 6,541,116, the entireties of which are hereby incorporated by reference. For example, possible coating materials include lubricious materials such as Teflon® and hydrophobic materials such as silicone lubricant dispersion PN 409 or hydrophilic materials such as hydrogel, or other lubricious coatings. The composition of the inner core and the outer layer and any additional layers, facilitate a desired flexibility and desired hardness for the tubular shaft member.

The materials of the inner core, outer layer as well as intermediate layer and exterior coating if provided, can vary and be any suitable material depending upon the desired need and use. The following table represents a few examples combinations of tables, although the disclosed subject matter is not limited to the following examples:

| Comb NO. | Outermost Layer | Second Layer | Third Layer | Innermost Layer |
|---|---|---|---|---|
| 1 | Pebax 72D | Primacor | HDPE | N/A |
| 2 | Pebax 63D | Primacor | HDPE | N/A |
| 3 | Pebax 72D | N/A | Nylon 12 | N/A |
| 4 | Pebax 63D | Pebax 72D | Primacor | HDPE |
| 5 | Pebax 63D | Nylon 12 | Primacor | HDPE |
| 6 | Pebax 55D | Tie layer | PET | Polyester |
| 7 | Polyester Elastomer | PET | Tie layer | HDPE |
| 8 | Pebax 63D | Nylon 6 | Primacor | HDPE |

The balloon member can comprise a plurality of suitable configurations including suitable materials and be a single layer or multi-layered balloon member. For example, the balloon member can be made from polyamides, polymeric material, including compliant, semi-compliant, or non-compliant polymeric material or polymeric blends, polyurethane material, a low tensile set polymer such as a silicone-polyurethane copolymer. Examples of other balloon and catheter embodiments which can be employed in accordance with the disclosed subject matter include U.S. Pat. Nos. 4,748,982; 5,496,346; 5,626,600; 5,300,085; 6,406,457; 6,500,148; 7,828,766 and U.S. Publication Nos. 2010/0030183; 2007/0088255; and 2010/0023108, each of which is hereby incorporated by reference in its entirety.

In accordance with another aspect of the disclosed subject matter, a therapeutic agent can be disposed on the balloon member 120. Examples of suitable therapeutic agents include anti-proliferative, anti-inflammatory, antineoplastic, anti-platelet, anti-coagulant, anti-fibrin, antithrombotic, antimitotic, antibiotic, antiallergic and antioxidant compounds. Such therapeutic agents can be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, and a retroviral vector.

In one embodiment, however, the therapeutic agents include a cytostatic drug. The term "cytostatic" as used herein means a drug that mitigates cell proliferation but allows cell migration. These cytostatic drugs, include for the purpose of illustration and without limitation, macrolide antibiotics, rapamycin, everolimus, zotaroliumus, biolimus, temsirolimus, deforolimus, novolimus, myolimus, structural derivatives and functional analogues of rapamycin, structural derivatives and functional analogues of everolimus, structural derivatives and functional analogues of zotarolimus and any marcrolide immunosuppressive drugs. The term "cytotoxic" as used herein means a drug used to inhibit cell growth, such as chemotherapeutic drugs. Some non-limiting examples of cytotoxic drugs include vincristine, actinomycin, cisplatin, taxanes, paclitaxel, and protaxel. Other drugs include dexamethasone, statins, sirolimus, and tacrolimus.

In addition to the therapeutic agent, any of a variety of fluid compositions can be applied to the expandable member. The fluid can include compounds or additives, such as polymers, binding agents, plasticizers, solvents, surfactants, additives, chelators, fillers, excipients, and the like, or combinations thereof. Suitable excipients, binding agents and other components include those described in detail in U.S. Publication No. 2011/0143014, which is hereby incorporated by reference in its entirety. In one embodiment, excipients include poly(ethylene glycol) (PEG), polyvinylpyrrolidone (PVP), polyoxyethylene sorbitan monooleate (tweens), poloxamer triblock copolymers of poly(ethylene oxide)-poly(propylene oxide)-poly(ethylene oxide) (Pluronics), carboxymethyl cellulose (CMC), and PEG phospholipids such as 1,2-distearolyl-sn-glycero-3-phosphoethanolamine-N-(methoxy(polyethylene glycol)-2000) (PEG-PE). In one embodiment, plasticizers include PEG, propylene glycol, N-methylpyrrolidone (NMP), glycerin, and tweens. Examples of possible compounds include zotarolimus, PVP and glycerol. In one embodiment the therapeutic agent can be provided in liquid form or dissolved in a suitable solvent. In another embodiment, the therapeutic agent is provided as a particulate and mixed in a suitable carrier for application as a fluid.

The fluid compositions, such as the therapeutic agents, can be applied to the expandable member using a variety of know techniques, such as spraying (air-atomization, ultrasonic, electrostatic, piezoelectric, etc.), spray drying, pneumatic spray, spray with patterning, electrospinning, direct fluid application, dip-coating, spin-coating, pipette coating, syringe coating, vapor deposition, roll coating, micro-droplet coating, ultrasonic atomization, or other means as known to those skilled in the art. The coating can be applied over at least a length or the entirety of the expandable member. By way of example, and not limitation, certain coating processes that can be used with the instant disclosed subject matter are described in U.S. Pat. No. 6,669,980 to Hansen; U.S. Pat. No. 7,241,344 to Worsham; U.S. Publication No. 2004/0234748 to Stenzel; and U.S. Publication No. 2011/028019 and U.S. patent application Ser. No. 13/280,067, the entire disclosures of which are hereby incorporated by reference. In accordance with one embodiment of the disclosed subject matter, the coating can be applied to either a folded or inflated balloon. Furthermore, the coating can be directly applied into the folds of the folded balloons. The coating characteristics are affected by process variables. For example, for dip-coating process, coating quality and thickness can vary as an effect of variables such as number, rate, and depth of dips along with drying time and temperature.

Figure 14:
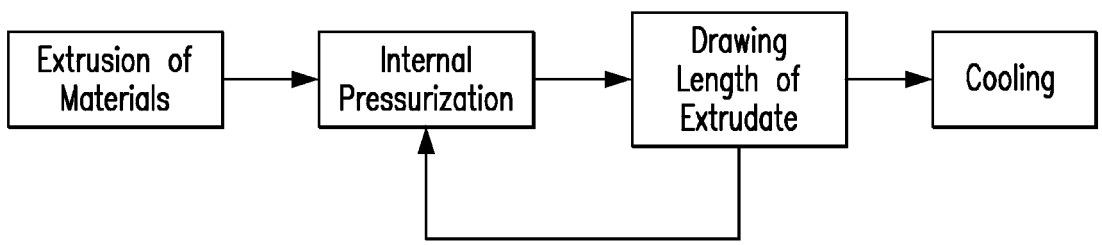
FIG. 14 is a block diagram of a method of forming a multi-lumen catheter, according to an embodiment of the disclosed subject matter.

A representative method of forming a multi-lumen catheter as described above is depicted in FIG. 14 for purpose of illustration and not limitation. For purpose of understanding, reference is made to the embodiments of FIGS. 1-13, although the method can be modified are appropriate to form other variations of the catheter shaft of the disclosed subject matter. The method includes extruding the first material to form an inner core 210 with the first lumen 212 and the second lumen 214 defined therein. The second material generally surrounding the first material can be simultaneously coextruded with or sequentially extruded over the inner core to form an extrudate having an outer layer 220 of the second material surrounding an inner core 210 of the first material. The first material and the second material each can be heated with a melt pump or the like, prior to the extrusion of the first and second materials. The stable flow of melting the first and second materials is controlled to maintain the dimensional stability of the extrudate.

The first lumen 212 and the second lumen 214 are internally pressurized and the extrudate is drawn by the application of an axial force while being cooled to a suitable temperature, such as by a water bath or the like. This drawing process generally increases length and reduces cross-sectional diameters, as well as aligns polymeric strands for increased strength as known in the art. However, unlike conventional techniques, the shape and size of first and second lumens can be maintained by internally pressurizing the lumens with suitable pressurized fluid, such as air or nitrogen. Hence as the outer cross-sectional dimension of the extrudate, and thus the inner core and/or outer layer, is reduced by the drawing process, the cross-sectional dimensions of the first and second lumens are maintained generally uniform along each respective length. Furthermore, and in accordance with an additional aspect of the disclosed subject matter, a length of the extrudate can be drawn at a varied speed to vary the outer cross-sectional dimension of the extrudate and thus the inner core and/or outer layer along the length thereof. In this manner, the spacing between the first lumen and second lumen likewise can decrease. A taper tube puller or the like can be used and controlled to draw the extrudate at a varied speed with the outer cross-sectional dimension and the extrudate decreasing proportionally with increasing speed and force applied.

As previously noted, the first lumen and the second lumen are respectively internally pressurized while drawing the extrudate to maintain a cross-section of the first lumen and a cross-section of the second lumen. As embodied herein, when varying the drawing speed or force, internal pressurization of the first lumen and the second lumen is adjusted proportionally to maintain the generally uniform size and shape thereof. For example, with increasing drawing speed or force, the pressured fluid is likewise increased to compensate for the increase in radially compressive force applied by the material of the inner core and/or outer layer. The adjustments to the pressured fluid can be synchronized with the drawing speed or force or can be controlled to adjust automatically to any change in drawing speed or force, such as by a controller.

In another embodiment, the extrudate can be vacuum sized by using a manifold with a series of outlets to create the vacuum atmosphere. For example, the vacuum sizing can be performed as an internal air method, can be used to determine the outer diameter of the tubing, and can provide a suitable surface finish, reduction in internal stress, and suitable dimension stability. The reference, *Plastics Extrusion Technology Handbook*, Second Edition, 1989, by Sidney Levy and James F. Carley, discusses further examples of vacuum sizing and the disclosure of which is herein incorporated by reference in its entirety.

Cooling of the extrudate is completed to form the monolithic elongate tubular shaft member 110 having a proximal end, a distal end and a longitudinal length therebetween. The tubular shaft member thus has an outer cross-sectional dimension that varies along the length of the tubular shaft member. The monolithic elongate tubular shaft member can be further cooled with an air box, and trimmed or cut as needed to the desired length of the tubular shaft member.

For purpose of illustration, a plurality of multi-lumen shaft members can be made sequentially along an inline assembly system. For example, catheters having a length of 185 cm or less by continuously cycling between increasing and decreasing drawing speeds, with intervals of constant speed therebetween as needed. Each cycle of increasing drawing speed or force results in a length of decreasing cross-sectional dimension of the extrudate, and thus the shaft member, while each cycle of decreasing speed in force results in a length of increasing cross-sectional dimension. The lumens are maintained at generally uniform size and shape by controlling pressurized fluid accordingly. In this manner, each subsequent length of the tubular member can be a mirror of the previous length, or can be constructed inline in rapid succession. This processing eliminates waste of the material for the tubular shaft member. The speed of the drawing can be further adjusted to allow for the formation of each proximal section, intermediate section, and distal section as desired. Once a respective catheter is created of a desired length, the speed of the assembly system is adjusted to create an adjacent catheter on the assembly. The cooled extrudate can subsequently be cut at the desired length by a cutting device and system. Rather than cycling the drawing process as described to form mirror or reverse tubular shaft lengths, each cycle can be repeated in sequence.

While the disclosed subject matter is described herein in terms of certain embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the various embodiments depicted and claimed, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

Many modifications, variations, or other equivalents to the specific embodiments described above will be apparent to those familiar with the art. It is intended that the scope of this disclosed subject matter be defined by the claims below and those modifications, variations and equivalents apparent to

What is claimed is:

1. A multi-lumen catheter comprising:
a monolithic elongate tubular shaft member having a proximal end, a distal end and a longitudinal length therebetween, the tubular shaft member having an outer cross-sectional dimension that varies along the length of the tubular shaft member,
the tubular shaft member having an inner core made of a first material and an outer layer made of a second material, the inner core having a first lumen and a second lumen defined therein, wherein the first lumen is disposed adjacent to the second lumen,
the first lumen having a first lumen cross-sectional dimension and a length extending at least along a portion of the length of the tubular shaft member, the first lumen cross-sectional dimension being substantially uniform along the length of the first lumen, and
the second lumen having a second lumen cross-sectional dimension and a length extending along the length of tubular shaft member, the second lumen cross-sectional dimension being substantially uniform along the length of the second lumen.

2. The catheter according to claim 1, wherein the outer cross-sectional dimension decreases distally along at least a portion of the tubular shaft member.

3. The catheter according to claim 1, wherein the outer cross-sectional dimension changes uniformly along at least a portion of the tubular shaft member.

4. The catheter according to claim 1, wherein the inner core has an outer cross-sectional dimension that varies along the length of the tubular shaft member.

5. The catheter according to claim 1, wherein the first lumen has a substantially circular cross-section configured to receive a guidewire therethrough.

6. The catheter according to claim 1, wherein the length of the first lumen extends the length of the tubular shaft member, the first lumen having a distal port at the distal end of the tubular shaft member and a proximal port at the proximal end of the tubular shaft member.

7. The catheter according to claim 1, further comprising a liner along at least a portion of the length of the first lumen.

8. The catheter according to claim 1, wherein the inner core and the outer layer are coextruded.

9. The catheter according to claim 1, wherein the first material is different from the second material.

10. The catheter according to claim 1, wherein the first material comprises at least one of Nylon, Nylon 12, Nylon TR55, transparent amorphous nylon, PEBAX, and high density polyethylene.

11. The catheter according to claim 1, wherein the second material comprises at least one of Pebax 63D, Pebax 70D, and Pebax 72D.

12. The catheter according to claim 1, wherein the outer cross-sectional dimension of the inner core decreases distally along the tubular shaft member and the outer layer includes an outer cross-sectional dimension that decreases distally along the tubular shaft member.

13. The catheter according to claim 1, wherein the first lumen has a distal port at the distal end of the tubular shaft member and a proximal port defined through an external surface of the tubular shaft member and spaced distally from the proximal end of the tubular shaft member.

14. The catheter according to claim 13, wherein the proximal port is defined by a notch extending through the outer layer and into the inner core to intersect the first lumen.

15. The catheter according to claim 1, wherein the tubular shaft member has a proximal section, an intermediate section, and a distal section, and further wherein the outer cross-sectional dimension varies along at least one of the proximal section, the intermediate section and the distal section.

16. The catheter according to claim 15, wherein the outer cross-sectional dimension is substantially uniform along at least one of the proximal section, the inter mediate section and distal section.

17. The catheter according to claim 16, wherein the outer cross-sectional dimension is uniform in the proximal section and in the distal section, and the outer cross-sectional dimension tapers in the intermediate section.

18. The catheter according to claim 1, further comprising a balloon member coupled to the tubular shaft member proximate the distal end thereof, the second lumen having a distal flow port in fluid communication with an interior chamber of the balloon.

19. The catheter according to claim 18, further comprising a distal flow port in fluid communication with the second lumen and disposed within the interior of the balloon.

20. The catheter according to claim 19, wherein the distal flow port is spaced proximally from the distal end of the tubular member, the distal flow port defined by a notch extending through the outer layer and into the inner core to intersect the second lumen.

21. The catheter according to claim 1, further comprising an intermediate layer between the inner core and the outer layer.

22. The catheter according to claim 21, wherein the intermediate layer is a tie layer to join the outer layer to the inner core.

23. The catheter according to claim 22, wherein the intermediate layer comprises at least one of Primacor, PET, Polyester Elastomer, and high density polyethylene.

24. The catheter according to claim 1, wherein the second lumen has at least one of a substantially semicircular cross-section or a substantially circular cross-section.

25. The catheter according to claim 24, wherein the second lumen comprises a plurality of individual inflation lumens.

26. The catheter according to claim 24, wherein the second lumen comprises the substantially semicircular cross-section and the substantially semi-circular cross-section of the second lumen has a straight edge portion proximate the first lumen.

27. The catheter according to claim 26, wherein the second lumen includes a proximal flow port proximate the proximal end of the tubular shaft member, the proximal flow port in fluid communication with the second lumen to receive a pressurized fluid therein.

28. The catheter according to claim 27, further comprising an adaptor coupled to the tubular member, the adaptor having a fluid branch fluidly coupled with the proximal flow port.

29. A method of forming a multi-lumen catheter comprising:
extruding a first material to form an inner core with a first lumen and a second lumen defined therein, wherein the first lumen is disposed adjacent to the second lumen, the first lumen having a first lumen cross-sectional dimension and the second lumen having a second lumen cross-sectional dimension;
extruding a second material generally surrounding the inner core to form an extrudate having an outer layer of the second material surrounding the inner core of the first material, the extrudate having an outer cross-sectional dimension;

drawing a length of the extrudate at a varied speed to vary the outer cross-sectional dimension along the length thereof; and internally pressurizing the first lumen and the second lumen, respectively, while drawing the extrudate to maintain the first lumen cross-sectional dimension and the second lumen cross-sectional dimension; and cooling the extrudate to form a monolithic elongate tubular shaft member having a proximal end, a distal end and a longitudinal length therebetween, the tubular shaft member having an outer cross-sectional dimension that varies along the length of the tubular shaft member.

30. The method of forming a multi-layer catheter according to claim 29, wherein internally pressurizing the first lumen and the second lumen is adjusted proportionally to draw the length of the extrudate at a varied speed.

31. The method of forming a multi-layer catheter according to claim 29, wherein internally pressurizing the first lumen and the second lumen is increased when drawing the length of the extrudate is increased.

32. The method of forming a multi-layer catheter according to claim 29, wherein extruding the first material and the extruding the second material is performed at least one of simultaneously or sequentially.

* * * * *